United States Patent
Do et al.

(10) Patent No.: US 11,938,113 B2
(45) Date of Patent: Mar. 26, 2024

(54) EPIGALLOCATHECHIN GALLATE SOLUTION

(71) Applicants: ASSISTANCE PUBLIQUE—HOPITAUX DE PARIS, Paris (FR); UNIVERSITE PARIS-SACLAY, Gif-sur-Yvette (FR)

(72) Inventors: Bernard Do, Issy-les-Moulineaux (FR); Muriel Paul, Montevrain (FR); Alain Astier, Paris (FR)

(73) Assignees: ASSISTANCE PUBLIQUE—HOPITAUX DE PARIS, Paris (FR); UNIVERSITE PARIS-SACLAY, Gif-sur-Yvette (FR)

( * ) Notice: Subject to any disclaimer, the term of this patent is extended or adjusted under 35 U.S.C. 154(b) by 849 days.

(21) Appl. No.: 16/766,175

(22) PCT Filed: Nov. 21, 2018

(86) PCT No.: PCT/EP2018/082029
§ 371 (c)(1),
(2) Date: May 21, 2020

(87) PCT Pub. No.: WO2019/101777
PCT Pub. Date: May 31, 2019

(65) Prior Publication Data
US 2020/0375939 A1 Dec. 3, 2020

(30) Foreign Application Priority Data

Nov. 23, 2017 (EP) .................................. 17306623

(51) Int. Cl.
| | | |
|---|---|---|
| *A61K 31/352* | (2006.01) | |
| *A61K 8/362* | (2006.01) | |
| *A61K 8/49* | (2006.01) | |
| *A61K 8/60* | (2006.01) | |
| *A61K 47/12* | (2006.01) | |
| *A61K 47/26* | (2006.01) | |
| *A61Q 19/00* | (2006.01) | |

(52) U.S. Cl.
CPC ............ *A61K 31/352* (2013.01); *A61K 8/362* (2013.01); *A61K 8/498* (2013.01); *A61K 8/60* (2013.01); *A61K 47/12* (2013.01); *A61K 47/26* (2013.01); *A61Q 19/00* (2013.01)

(58) Field of Classification Search
CPC ...... A61K 31/352; A61K 8/362; A61K 8/498; A61K 8/60; A61K 47/12; A61K 47/26; A61Q 19/00
See application file for complete search history.

(56) References Cited

U.S. PATENT DOCUMENTS

2014/0088030 A1 3/2014 Auriol et al.
2015/0250221 A1 9/2015 Patel et al.

FOREIGN PATENT DOCUMENTS

| CN | 101744807 A | | 6/2010 |
|---|---|---|---|
| CN | 104719910 | * | 6/2015 |
| CN | 104800850 A | | 7/2015 |
| WO | WO 2007/059953 | * | 5/2007 |
| WO | 2014/055830 A1 | | 4/2014 |
| WO | 2015/136551 A1 | | 9/2015 |

OTHER PUBLICATIONS

Krupkova et al. J Nutr Biochem, 37, 1-12, 2016. (Year: 2016).*
Dorr et al., WO 2007/059953, published: May 31, 2007, English machine translation obtained on Feb. 10, 2023. (Year: 2023).*
Zhang et la. CN 104719910; ENglish machine translation obtained on Sep. 22, 2023. (Year: 2023).*
Peters, C., et al., "Formulation with ascorbic acid and sucrose modulates catechin bioavailability from green tea," Food Research International, vol. 43, 2010, pp. 95-102.
Shpigelman, A., et al., "Mechanisms of saccharide protection against epigallocatechin-3-gallage deterioration in aqueous solutions," Food Chemistry , vol. 139, 2013, pp. 1105-1112.
European Search Report and Written Opinion for European Patent Application No. 17306623.4, dated May 4, 2018.
International Search Report and Written Opinion for International Patent Application No. PCT/EP2018/082029, dated Feb. 5, 2019.
Afzal M., et al., "Green tea polyphenols and their potential role in health and disease, " Inflammopharmacol 23, 2015, pp. 151-161.
Cabrera, C., et al., "Beneficial Effects of Green Tea-A Review," Journal of the American College of Nutrition, vol. 25, No. 2, May 2006, pp. 79-99.
Chow, H-H. S., et al. "Effects of Dosing Condition on the Oral Bioavailability of Green Tea Catechins after Single- Dose Administration of Polyphenon E in Healthy Individuals," Cancer Prevention, Clin Cancer Research, 11(12), Jun. 15, 2005, pp. 4627-4633.
Krupkova, O., et al., "Stability of (−)-epigallocatechin gallate and its activity in liquid formulations and delivery systems," Journal of Nutritional Biochemistry 27, 2016, pp. 1-12.
Mata-Bilbao, M-D-L., et al., "A New LC/MS/MS Rapid and Sensitive Method for the Determination of Green Tea Catechins and their Metabolites in Biological Samples," J. Agric. Food Chem., 55, 2007, pp. 8857-8863.
Nichols, J., et al., "Skin photoprotection by natural polyphenols: Anti-inflammatory anti-oxidant and DNA repair mechanisms," Arch Dermatol Res., 302(2), Mar. 2010, 19 pages.
Pharmacopee Europeenne, Drogues vegetales, Plantae Mediciniales, 2017, pp. 935-936. (English Translation Not Available).
Shin, S., et al., "Protective Effect of (−)-Epigallocatechin Gallate against Photo-Damage Induced by Ultraviolet A in Human Skin Fibroblasts," Tropical Journal of Pharmaceutical Research, 13(7), Jul. 2014, pp. 1079-1084.

(Continued)

*Primary Examiner* — Genevieve S Alley
(74) *Attorney, Agent, or Firm* — Greer, Burns & Crain, Ltd

(57) ABSTRACT

A stable pharmaceutical or dermo-cosmetic aqueous solution of epigallocatechin gallate is provided. The present solution has improved EGCG solubility, stability and bioavailability.

16 Claims, 7 Drawing Sheets

(56) References Cited

OTHER PUBLICATIONS

Figure 1:
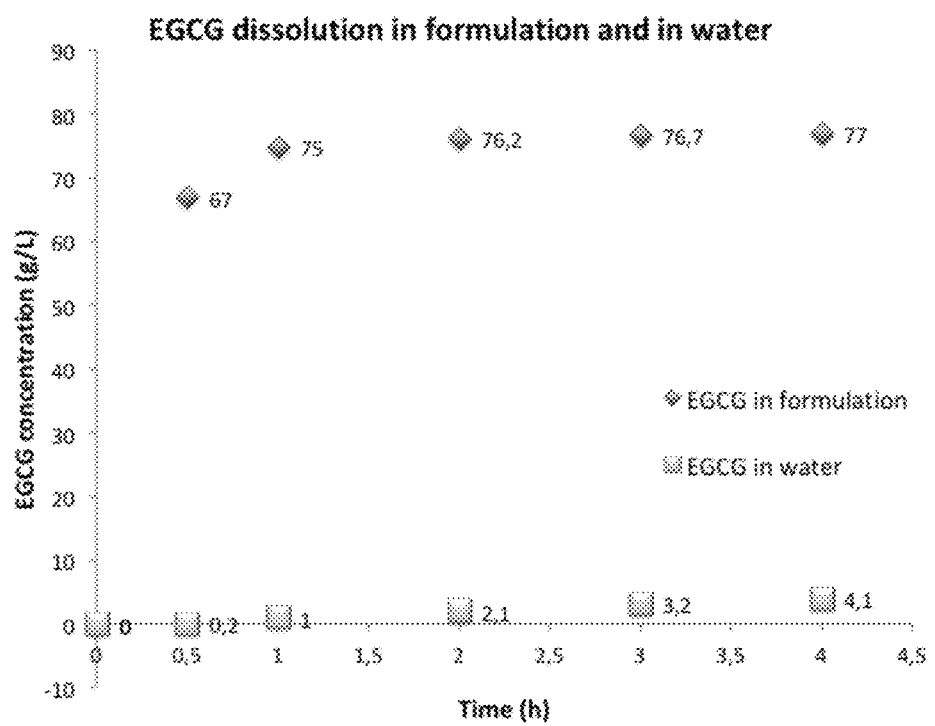

Vayalil, P., et al., "Treatment of green tea polyphenols in hydrophilic cream prevents UVB-induced oxidation of lipids and proteins, depletion of antioxidant enzymes and phosphorylation of MAPK proteins in SKH-1 hairless mouse skin," Carcinogenesis, vol. 24, No. 5, 2003, pp. 927-936.

Yang, C., et al., "Cancer prevention by tea: animal studies, molecular mechanisms and human relevance," Nature Reviews, Cancer, vol. 9, Jun. 2009, pp. 429-439.

Zhang, L., et al., "Investigation of intestinal absorption and disposition of green tea catechins by Caco-2 monolayer model," International Journal of Pharmaceutics 287, 2004, pp. 1-12.

Pharmacopee Europeenne, Drogues vegetales, Plantae Mediciniales, monograph 1433, 2017, pp. 935-936. (English Machine Translation Provided).

* cited by examiner

EPIGALLOCATHECHIN GALLATE SOLUTION

The present invention concerns a stable pharmaceutical or dermo-cosmetic aqueous solution comprising epigallocathechin gallate.

Green tea (*Camellia sinensis*) has been widely consumed in China and other Asian countries for several millennia. It is considered as one of the most promising nutrients for the prevention and/or treatment of many diseases (Cabrera, Artacho et al., *Journal of the American College of Nutrition*, Vol. 25, No. 2, 79-99 (2006)). Green tea contains a high amount of polyphenols. Polyphenolic catechins are well known for their potent antioxidant properties, which make them candidates for development of drugs covering large therapeutic domains. Most polyphenols present in green tea are flavanols, commonly called catechins (Afzal, Safer et al., *Inflammopharmacology*. 2015 August; 23 (4):151-61).

The antioxidant properties of green tea catechins were examined in a number of in vitro and in vivo models. Experimental results and clinical studies provided convincing data on the beneficial effect of tea extracts and tea polyphenols (Yang, Wang et al. *Nat Rev Cancer.* 2009 June; 9 (6): 429-439). Catechins are particularly described as having anticancer effects and protective properties against neurodegenerative diseases such as Parkinson's disease and Alzheimer's disease.

Epigallocatechin gallate (EGCG), by far the most abundant of green tea catechin polyphenols, has been recognized for its tremendous potential in preventing or slowing aging-related diseases such as cancer, diabetes and tissue degeneration (Krupkova et al. *Journal of Nutritional Biochemistry* 37 (2016) 1-12).

EGCG has been shown to prevent, in vitro and in vivo, oxidative damage and depletion of antioxidant enzymes caused by exposure to solar UV radiation (Vayalil et al. *Carcinogenesis* 24 (2003) 927-936). Topical treatments with EGCG have been found to decrease the skin inflammatory response due to sun exposure by inhibiting inflammatory leukocyte infiltration and prostaglandin metabolite production (Nichols et Katiyar, *Dermatol Arc. Res.* 302 (2010) 71-83). In addition, EGCG has been reported to protect against sunlight-induced suppression of the cutaneous immune system and to prevent photo-aging of the skin by reducing the expression of matrix metallo-proteinases triggered by solar UV radiation (Shin et al., *Tropical Journal of Pharmaceutical Research* (2014) 13 (7): 1079-1084)

EGCG is of natural origin and is contained in green tea extract. Its content varies according to the season, the type of leaves and the part of the plant used. The dry extracts of green tea contain about 35% of polyphenols, 30% of which are due to catechins, which themselves contain 55-80% of EGCG.

EGCG is currently available as herbal drugs or green tea extracts (*monograph* 1433, current *European Pharmacopoeia; monograph* 2668, *Pharmeuropa* June 2017), isolated or not. Tea brewages and the capsules or tablets co-formulated with vitamins account for the main paths for EGCG intake.

Despite the fact that EGCG exhibits remarkable antioxidant properties, only limited effects have been observed in animals and human epidemiological studies. After oral administration, the bioavailability of EGCG was found to be very low in humans, resulting in plasma concentrations 5 to 50 times less than concentration shown to exert biological activities in in vitro systems (Chow et al., *Clin Cancer Res* 11 (2005) 4627-4633).

Like the other catechins, EGCG suffers from poor solubility and low skin permeability.

Poor biopharmaceutical properties of EGCG are mainly due to its relative low solubility in water, low chemical stability, low permeability and a short plasma half-life.

Indeed, at normal condition EGCG is soluble only at a rate of 4.6 g/L (10 mM). The quantity of soluble EGCG is far from sufficient for developing a pharmaceutical product, which needs a high concentration of active ingredient in a small volume.

EGCG is prompt to react by auto-oxidation and thus exhibits very low chemical stability. Auto-oxidation of EGCG yields reactive oxygen species capable of inducing polymerization and decomposition of EGCG. The resulting quinone derivatives, dimers or oligomers have much lower intestinal absorption rates.

In general, its immediate environment, such as the presence of water, pH, temperature, oxygen content, antioxidant levels and metal ions, even in trace amounts (iron, zinc, copper, aluminium) directly affects its stability (Krupkova et al., *Journal of Nutritional Biochemistry* 37 (2016) 1-12).

By the way, the low bioavailability is also due in part to its interactions with nutrients present, including co-formulated excipients. Indeed, studies have shown that commonly sparingly soluble components of the capsule and those of the gelatin shell itself can combine with EGCG after disintegration and form even less soluble complexes which impede absorption.

Above-mentioned drawbacks also prevent EGCG to be used in skin care products. Besides of its chemical instability, poor skin permeability, low solubility in water, EGCG, is very sensitive to ultra violet irradiation. EGCG was found to decompose by 70%, after 1-h ultra violet irradiation. Because EGCG is a very useful ingredient for protection of the skin against the damaging effects of solar radiation, its stabilization under exposure to ultra violet irradiation is of paramount importance for the preparation of effective dermatological products containing EGCG.

In order to improve the solubility and stability of EGCG in the context of topical administration, several technologies have been proposed in the past. However, EGCG formulations described to this day still cannot completely meet the requirements for clinical development of EGCG.

US20140088030 described a method for producing O-α-glucoside derivatives of phenolic compounds (such as EGCG), by incubating sucrose and a glucansucrase from *Leuconostoc* species with the phenolic compounds. However, this method involves structural changes of EGCG. These changes may impair other properties of EGCG.

Nanoparticles encapsuling EGCG have also been developed to promote the sustained release of green tea polyphenol concentrates in the gastrointestinal tract (Krupkova et al., *Journal of Nutritional Biochemistry* 37 (2016) 1-12). However, changes in release rates and kinetics could make the EGCG biopharmaceutical phase even more complex and far less predictable. By the way, for equivalent doses administered, it is possible that the use of a form gradually releasing EGCG, which is therefore present at smaller doses in the gastrointestinal tract, would expose it more to enzymatic degradations and bacterial metabolisms than an immediate release form.

Krupkova et al. (*Journal of Nutritional Biochemistry* 37 (2016) 1-12) described a solution formulation of green tee catechins (GTC) comprising 1.09 mM of a GTC mixture, 0.15 g/mL of sucrose and 2 mg/mL of citric acid. However, a 6-month assessment revealed that addition of sucrose had little effect on the stability of GTC, whereas addition of citric acid destabilized GTC.

There is a serious need to develop an EGCG-containing pharmaceutical or dermo-cosmetic product having improved solubility and stability, easy to be formulated, and exempt of excipient or ingredient which can form insoluble complex with EGCG.

The objective of the invention has been to develop a new galenic formulation of epigallocatechin gallate (EGCG) wherein ECGC has a better water solubility and stability.

The first aspect of the present invention concerns a stable pharmaceutical or dermo-cosmetic aqueous solution of epigallocatechin gallate, said solution comprising:
13-107 mg/ml of epigallocatechin gallate,
At least one disaccharide,
0.1-1.0 mmol/l of at least one chelating agent,
A pharmaceutically acceptable or dermo-cosmetically acceptable pH-modifying agent,
wherein said solution is at a pH in a range of 3.0 to 4.0 and the molar ratio of epigallocatechin gallate/disaccharide is from 0.1 to 0.8, particularly 0.25.

In one embodiment, the present invention concerns a stable pharmaceutical aqueous solution of epigallocatechin gallate, said solution comprising:
13-107 mg/ml of epigallocatechin gallate,
At least one disaccharide,
0.1-1.0 mmol/l of at least one chelating agent,
A pharmaceutically acceptable pH-modifying agent,
wherein said solution is at a pH in a range of 3.0 to 4.0 and the molar ratio of epigallocatechin gallate/disaccharide is from 0.1 to 0.8, particularly 0.25.

In a particular embodiment, said stable solution is for its use in the preparation of a dermo-pharmaceutical product.

Another embodiment of the present invention concerns a dermo-cosmetic aqueous solution of epigallocatechin gallate, said solution comprising:
13-107 mg/ml of epigallocatechin gallate,
At least one disaccharide,
0.1-1.0 mmol/l of at least one chelating agent,
A cosmetically acceptable pH-modifying agent,
wherein said solution is at a pH in a range of 3.0 to 4.0 and the molar ratio of epigallocatechin gallate/disaccharide is from 0.1 to 0.8, particularly 0.25.

Against all odds, without resorting to temperature and organic solvents such as DMSO, the Inventors of the present invention have successfully increased nearly 20 times EGCG concentration in aqueous solution in the presence of a disaccharide.

Moreover, it is observed that this aqueous solution can be stable at 2-8° C. and at ambient temperature during 18-24 months and 9-12 months, respectively.

It has been observed by the Inventors for the first time that EGCG and disaccharide, when they are present in certain range of molar ratio and in aqueous solution, can form a complex wherein hydrogen bonds are formed between hydroxyl groups of EGCG and those of disaccharide as acceptor.

Without being bounded by any theory, it is supposed that the forming of EGCG/disaccharide complex and hydrogen bond make it possible to substantially increase EGCG solubility in aqueous solution, which in turn result in an increase of solution stability by:
decreasing the dissolved oxygen content,
increasing the ratio substratereagent making the reactions less quantitative,
better auto-protection of EGCG by auto-quenching and quenching of singlet oxygen.

By the way, hydrogen bond formed between EGCG and disaccharide would prevent the ester function from being exposed to hydrolysis reagents.

Thanks to high concentration of soluble EGCG and high stability, said pharmaceutical solution can display an improved bioavailability of EGCG compared to EGCG formulations known up to date, since the high concentration of EGCG can avoid progressive dissolution of EGCG linked to low substrate/reagent ratio, favourite the passage of the intestinal barrier and limit hepatic clearance of EGCG which is known to be important.

By the term "a stable pharmaceutical or dermo-cosmetic aqueous solution of epigallocatechin gallate" is herein meant to a pharmaceutical or dermo-cosmetic solution which conserves at least 95% (w/w) of EGCG and its trans-epimer, gallocatechin gallate (GCG), compared to initial EGCG quantity in said solution after at least 9 months of storage at room temperature from 20 to 25° C. or at least 18 months of storage from 2 to 8° C.

The pharmaceutical solution of the invention is pharmaceutically acceptable, i.e. do not produce an adverse, allergic or other untoward reaction when administered to a patient.

As used herein, the term "epigallocatechin gallate" in the present invention means natural EGCG purified from any part of leaves of *Camellia sinensis* picked at any seasons.

Preferably, any extract of EGCG having a content of at least 90%, particularly at least 95%, more particularly at least 97%, by weight of EGCG is suitable for preparing a solution of the present invention.

Preferably, the extract of EGCG used for preparing a solution of the present invention satisfies the requirements specified in concerned current *European pharmacopoeia* (*monographs* 1433 and 2668, current *European Pharmacopoeia*).

The term "disaccharide" means sugars formed from condensation of two monosaccharides which are joined by glycosidic linkage.

In a preferred embodiment, said disaccharide is a disaccharide easily soluble in water which has a solubility higher than 100 mg/ml in 25° C.

In a more preferred embodiment, said disaccharide is sucrose or trehalose.

As used herein, the term "chelating agent" refers to a chemical compound that reacts with metal ions to form stable, water-soluble metal complexes. In a pharmaceutical solution of the present invention, the presence of chelating agents is aimed at capturing any trace metal ions potentially present in the solution and preventing EGCG deprotonation which can be catalysed in the presence of metal ions even at trace concentration.

Examples of suitable chelating agent for a solution of the present invention are citric acid, calcium disodium edetate, disodium edetate, fumaric acid, malic acid, maltol and pentetic acid.

The pH of a solution of the present invention is maintained in a range of pH 3.0 to 4.0 to avoid risk of degradation of the EGCG linked to loss of a proton at higher pH (>5.0).

In a preferred embodiment of the present invention, the pharmaceutical or dermo-cosmetic solution of the present invention has a pH in a range of 3.0 to 3.5.

The pH of the solution may be adjusted by the incorporation of a suitable pharmaceutically or dermo-cosmetically acceptable pH-modifying agent.

The term "pharmaceutically acceptable pH-modifying agent" refers to any chemical agents which are, within the scope of sound medical judgment, suitable for use in contact with the tissues of humans without undue toxicity, irritation, allergic response and the like.

The term "dermo-cosmetically acceptable pH-modifying agent" refers to any chemical agents, which are non-toxic for use in a dermo-cosmetic product.

The term "dermo-cosmetic product" is meant to a product to be put in contact with different superficial parts of the human body, especially the epidermis, hair, nails, lips, etc., said product combines a cosmetic action with a dermatological action.

Generally, the pH-modifying agent can be an acidifying agent, especially an acid. Any suitable pharmaceutically acceptable acid may be used in the pharmaceutical solution of the present invention. Any suitable dermo-cosmetically acceptable acid may be used in the dermo-cosmetic solution of the present invention.

Sometimes, it may be necessary to incorporate a buffering agent to increase the pH of the solution to reach desired pH range. Any suitable pharmaceutically or dermo-cosmetically acceptable buffering agent may be respectively used in a pharmaceutical or dermo-cosmetic solution of the present invention.

In an embodiment of the present invention, the pH-modifying agent is chosen from acetic acid, adipic acid, ammonium carbonate, ammonium hydroxide, ammonium phosphate, citric acid, diethanolamine, fumaric acid, hydrochloric acid, malic acid, nitric acid, proprionic acid, potassium acetate, potassium bicarbonate, potassium chloride, potassium citrate, potassium metaphosphate, potassium phosphate, sodium acetate, sodium bicarbonate, sodium carbonate, sodium citrate, sodium glycolate, sodium hydroxide, sodium lactate, sodium phosphate, sodium proprionate, succinic acid, sulfuric acid, tartaric acid, triethanolamine, or mixtures thereof.

The quantity of pH-modifying agent required is that which can confer to the solution the desired pH.

According to an embodiment of the present invention, a chelating agent and a pH-modifying agent can be a same compound. For example, citric acid is on the same time a chelating agent and a pH-modifying agent.

According to an embodiment of the present invention, the pharmaceutical or dermo-cosmetic solution of the present invention further comprises at least one antioxidant agent suitable for the aqueous systems and compatible with acidic pH.

Examples of suitable antioxidant agent are ascorbic acid, erythorbic acid, monothioglycerol, sodium metabisulfite, sodium bisulfite, or reducing sugar.

The term "reducing sugar" is defined herein to include any saccharide that includes an aldehyde functional group or can isomerize to form an aldehyde functional group in basic solution, for example glucose, fructose, maltose, galactose, lactose and pentose sugars such as xylose.

In a preferred embodiment of the present invention, the antioxidant agent in a pharmaceutical or dermo-cosmetic solution of the present invention is glucose or fructose.

In a preferred embodiment, when the pharmaceutical or dermo-cosmetic solution of the present invention comprises an antioxidant chosen from ascorbic acid, erythorbic acid, monothioglycerol, sodium metabisulfite, or sodium bisulfite, the concentration of said antioxidant is in the range of from 0.01 mg/ml to 0.5 mg/ml.

In another preferred embodiment, when the pharmaceutical or dermo-cosmetic solution of the present invention comprises a reducing sugar, the concentration of said reducing sugar is at least 10 mg/ml, preferably no more than 500 mg/ml, more preferably at 100 mg/ml.

In a pharmaceutical solution of the present invention, the presence of an organic solvent is not necessary.

In a particular embodiment of the invention, said pharmaceutical solution is exempt of organic solvent.

Examples of organic solvents are acetone, acetonitrile, chloroform, dimethyl sulfoxide, ethanol, propylene, glycol, glycerol, PEG400.

In another particular embodiment of the invention, said pharmaceutical solution comprises an organic solvent chosen from ethanol, propylene glycol, glycerol, PEG 400.

In a particular embodiment, the present invention provides a pharmaceutical aqueous solution comprising or consisting of:
- 13-107 mg/ml, particularly 27-67 mg/ml, more particularly 27-53 mg/ml, of epigallocatechin gallate,
- 0.05-3.0 mg/ml, particularly 0.08-0.25 mg/ml, more particularly 0.10-0.20 mg/ml of citric acid,
- 25-140 mg/ml, particularly 50-125 mg/ml, more particularly 100-125, mg/ml of sucrose,
- Optionally, 25-250 mg/ml, in particular 100 mg/ml, of glucose and/or fructose.

In a still more particular embodiment, the present invention provides a pharmaceutical aqueous solution comprising or consisting of:
- 27 mg/ml of epigallocatechin gallate
- 0.1 mg/ml of citric acid
- 100 mg/ml of sucrose,
- 100 mg/ml of glucose.

In one embodiment of the present invention, the pharmaceutical solution is formulated as oral pharmaceutical composition, especially as drinking pharmaceutical composition.

Said solution can include one or more pharmaceutically acceptable sweetener, and/or aromatic agent. A sweetener or an aromatic agent is particularly useful when said pharmaceutical solution does not contain a glucose or a fructose as antioxidant agent.

Sweeteners may be included but not limited to aspartame, acesulfame-K, mannitol, sorbitol, lactitol, xylitol, erythritol or their mixtures thereof. Aromatic agent can be any fruit aromas, or other aromas such as cola flavour aromas, or their mixtures thereof.

The quantity of said sweetener or aromatic agent can be determined according to common knowledge in the field of drug formulation.

In another embodiment, the pharmaceutical solution of the invention is an injectable formulation, which can be administrated by parenteral routes, such as intravenous or subcutaneous administration, or by topical route.

A pharmaceutical solution of the present invention can be prepared according to any conventional methods for solution preparation. The ingredients should be added one after another after complete dissolution of each previously added ingredient. The dissolution of ingredients can be achieved under agitation at room temperature.

After complete dissolution of all ingredients, the solution can be subjected to one or several sterile filtrations and then filled into pharmaceutical containers, such as a multiple dose vial, at suitable volume.

In another particular embodiment, the present invention provides a dermo-cosmetic aqueous solution comprising or consisting of:
- 13-107 mg/ml, particularly 27-67 mg/ml, more particularly 27-53 mg/ml, of epigallocatechin gallate,
- 0.05-3.0 mg/ml, particularly 0.08-0.25 mg/ml, more particularly 0.10-0.20 mg/ml of citric acid, 25-140 mg/ml, particularly 50-125 mg/ml, more particularly 100-125, mg/ml of sucrose, Optionally, 25-250 mg/ml, in particular 100 mg/ml, of glucose and/or fructose.

In a still more particular embodiment, the present invention provides a dermo-cosmetic aqueous solution comprising or consisting of:

27 mg/ml of epigallocatechin gallate
0.1 mg/ml of citric acid
100 mg/ml of sucrose,
100 mg/ml of glucose.

Another aspect of the present invention provides a unit dose of epigallocatechin gallate comprising a pharmaceutical or dermo-cosmetic aqueous solution described before.

Compared to a solution of the present invention conditioned in bigger volume, such as in multiple dose vial, a pharmaceutical or dermo-cosmetic solution in unit dose offers more advantages for patients, in particular in the maintain of chemical stability of the solution.

Said unit dose of the present invention has a volume in the range of 5-30 ml, particularly 10-15 ml, more particularly 15 ml.

According to the invention, a unit dose of the solution comprises epigallocatechin gallate in a weight in the range of 200-1600 mg, particularly 400-1200 mg, more particularly 400 mg.

In a preferable embodiment, the unit dose of the present invention is in a volume of 5-30 ml, particularly 10-15 ml, more particularly 15 ml, which contains EGCG in a weight in the range of 200-1600 mg, particularly 400-1200 mg, more particularly 400 mg.

In a more preferable embodiment, the unit dose of the present invention is in a volume of 15 ml and contains 400 mg of EGCG and 1.5 g of sucrose.

Another aspect of the present invention concerns a solid composition resulting from any water removal process, especially lyophilisation or spray drying, of a pharmaceutical aqueous solution described before, or of a unit dose described before.

Said solid composition can be of crystalline, hydrate or anhydrous polymorph forms.

A pharmaceutical solution described before can be re-established from said solid composition by adding suitable volume of water.

The present invention provides a pharmaceutical composition comprising a pharmaceutical aqueous solution, a pharmaceutical aqueous solution in a unit dose, or a solid composition resulting from any water removal process of said pharmaceutical solution, or of said unit dose.

In a particular embodiment, said pharmaceutical composition of the invention is formulated to be used as a dermo-pharmaceutical product.

Said product can be a semi-solid or pasty topical composition resulting from mixing said dermo-cosmetic solution with different pasty or semi-solid bases.

The present invention provides a pharmaceutical aqueous solution, a pharmaceutical aqueous solution in a unit dose, or a solid composition resulting from any water removal process of said pharmaceutical solution, or of said unit dose, for its use as a medicament in the treatment of cancers, cardiovascular disorder, diabetes, neurodegenerative diseases, such as Parkinson's disease and Alzheimer's disease, or dermatological diseases.

The present invention provides also a dermo-cosmetic product comprising a dermo-cosmetic aqueous solution, a dermo-cosmetic aqueous solution in a unit dose, or a solid composition resulting from any water removal process of said dermo-cosmetic solution, or of said unit dose.

Said dermo-cosmetic product can be a semi-solid or pasty topical composition resulting from mixing said dermo-cosmetic solution or said solid composition with different pasty or semi-solid bases.

Said dermo-cosmetic product can be skin care products, such as sun creams, day creams, night creams, after-sun products, makeup's, lipsticks, eye cosmetics, shampoos, showers.

The present invention provides also a mixture formed by epigallocatechin gallate and a disaccharide, in particular sucrose, wherein the molar ratio of epigallocatechin gallate/disaccharide is from 0.1 to 0.8, in particular 0.25.

Said mixture ensures a best EGCG water dissolution rate at ambient temperature from 20° C. to 25° C.

The present invention concerns also an eutectic complex formed by EGCG and disaccharides, wherein EGCG and disaccharides are in a molar ratio of 0.7-0.85.

The term "eutectic complex" refers to a complex obtained after the melting at a specific temperature of two or more components in a specific range of molar ratio. In an eutectic complex, the components melt and solidify at a same temperature which is lower than melting temperature of each component.

In said complex, EGCG and disaccharides are bounded by hydrogen bonding.

According to a particular embodiment of the present invention, the eutectic complex is a complex formed by EGCG and sucrose wherein EGCG and sucrose are in a molar ratio of 0.7-0.85.

In a preferred embodiment, the eutectic complex EGCG/sucrose of the present invention has an eutectic temperature in the range of 80-90° C.

In another aspect, the present invention concerns a method for improving EGCG water solubility.

Said method comprises following steps:

(i) preparing a solution containing:
at least one disaccharide, in particular sucrose and trehalose, wherein the molar ratio of epigallocatechin gallate/disaccharide is from 0.1 to 0.8, particularly 0.25
0.1-1.0 mmol/l of at least one chelating agent,
a pharmaceutically acceptable pH-modifying agent to adjust the pH of solution in a range of 3.0 to 4.0,
optionally, at least one antioxidant agent suitable for the aqueous systems and compatible with acidic pH, (ii) dissolving 13-107 mg/ml, particularly 27-67 mg/ml, more particularly 27-53 mg/ml, of EGCG in the solution prepared in preceding step.

The present invention concerns also a method for improving EGCG bioavailability.

Said method comprises following steps:

(i) dissolving 13-107 mg/ml, particularly 27-67 mg/ml, more particularly 27-53 mg/ml, of EGCG in a solution containing:
at least one disaccharide, in particular sucrose and trehalose, wherein the molar ratio of epigallocatechin gallate/disaccharide is from 0.1 to 0.8, particularly 0.25
0.1-1.0 mmol/l of at least one chelating agent,
a pharmaceutically acceptable pH-modifying agent to adjust the pH of solution in a range of 3.0 to 4.0,
optionally, at least one antioxidant agent suitable for the aqueous systems and compatible with acidic pH, (ii) administrating said solution to a patient in need of treatment by EGCG.

In a preferred embodiment, when the antioxidant is chosen from ascorbic acid, erythorbic acid, monothioglycerol, sodium metabisulfite, or sodium bisulfite, the concentration of said antioxidant in aforementioned solution is in the range of from 0.01 mg/ml to 0.5 mg/ml.

In another preferred embodiment, when the pharmaceutical solution of the present invention comprises a reducing sugar, the concentration of said reducing sugar is at least 10 mg/ml, preferably no more than 500 mg/ml, more preferably at 100 mg/ml.

Administration can be carried out by oral administration or by parenteral routes.

The present invention is illustrated in more detail by the following figures and examples.

FIGURES

FIG. 1 shows solubility of EGCG in a solution containing 100 mg/mL of sucrose according to the invention (represented by diamond symbols) compared to that of EGCG alone in water (represented by square symbols). X-axe represents dissolution time (hours). Y-axe represents EGCG content in solution (g/L).

Figure 2A:
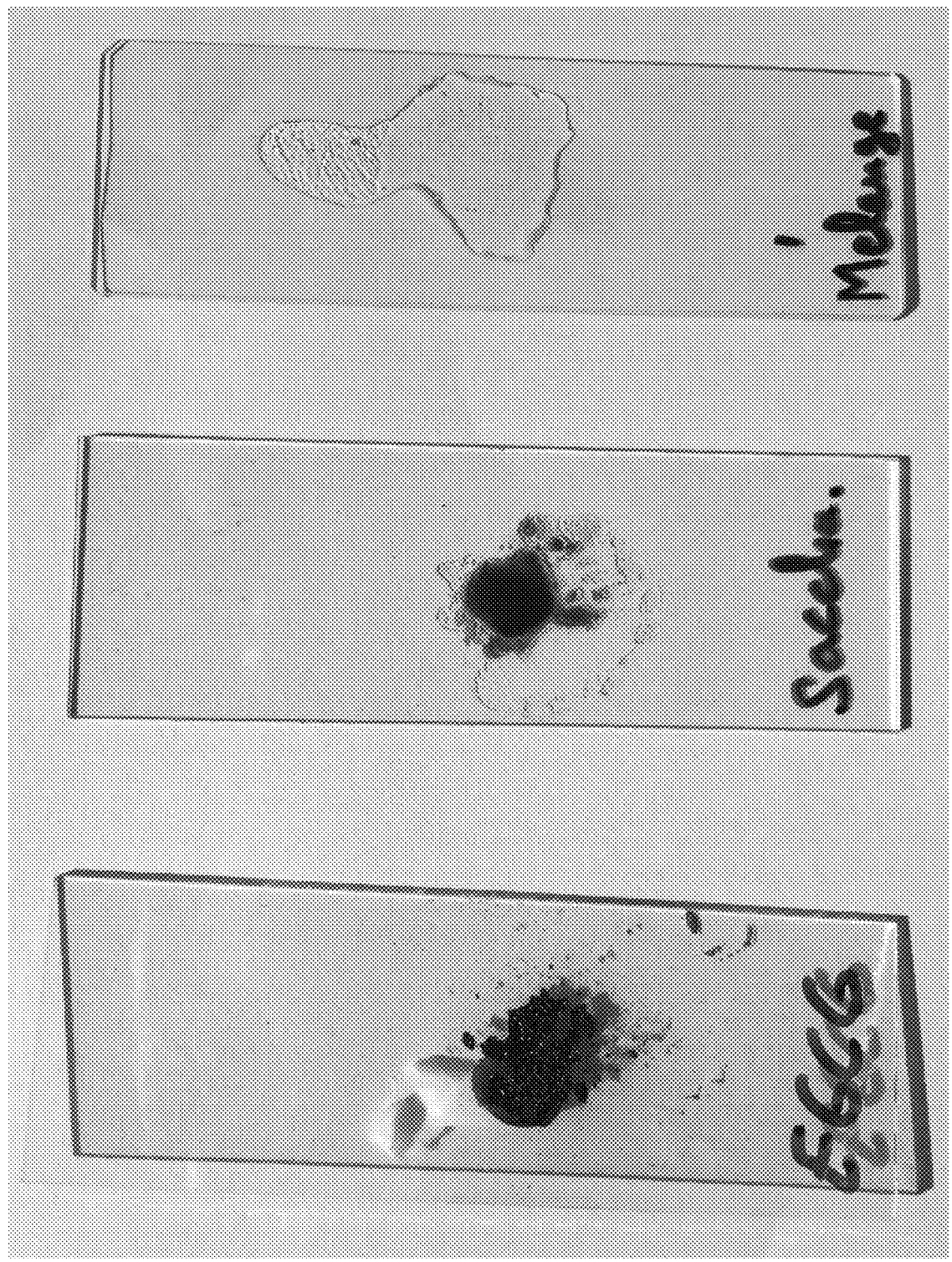
Figure 2B:
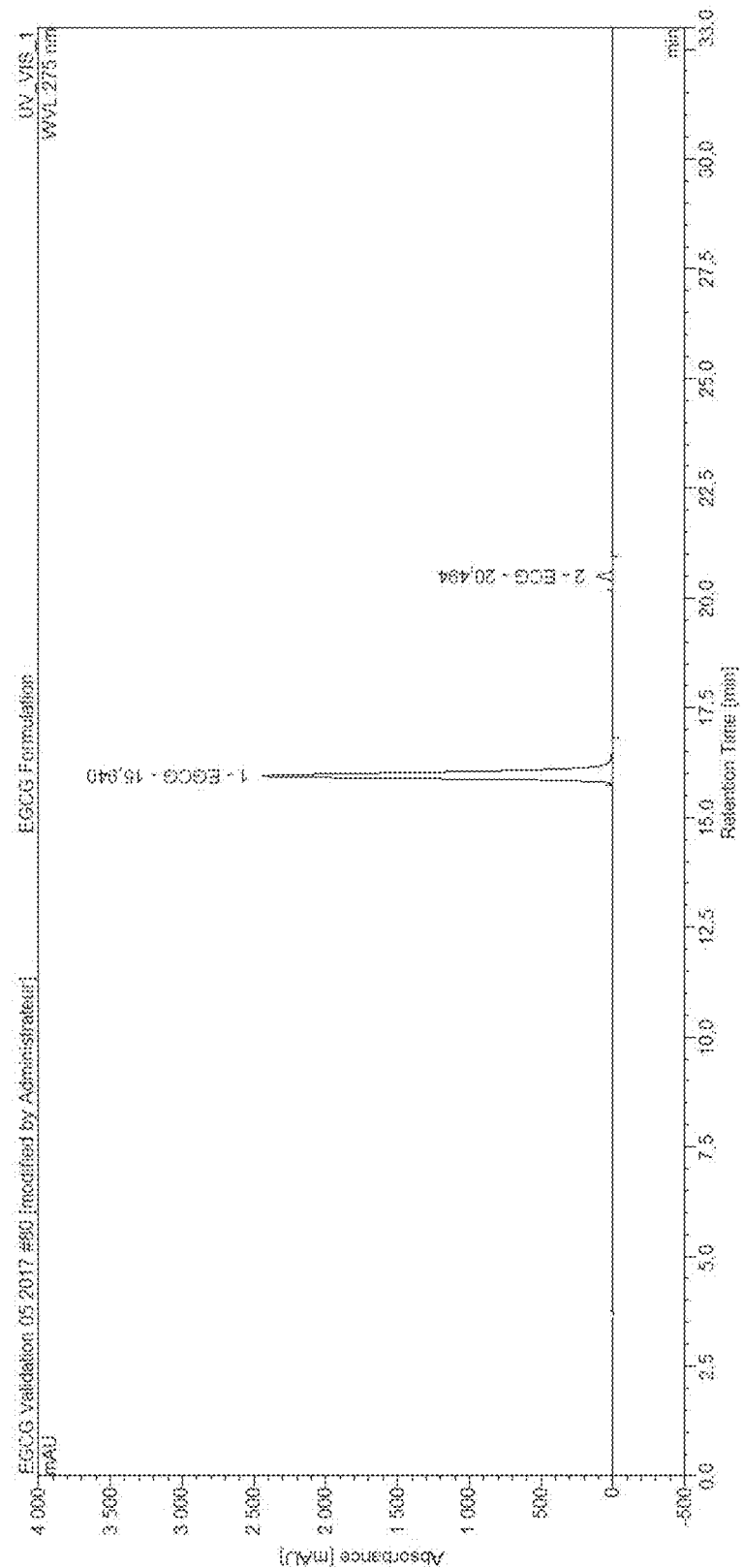
Figure 2C:
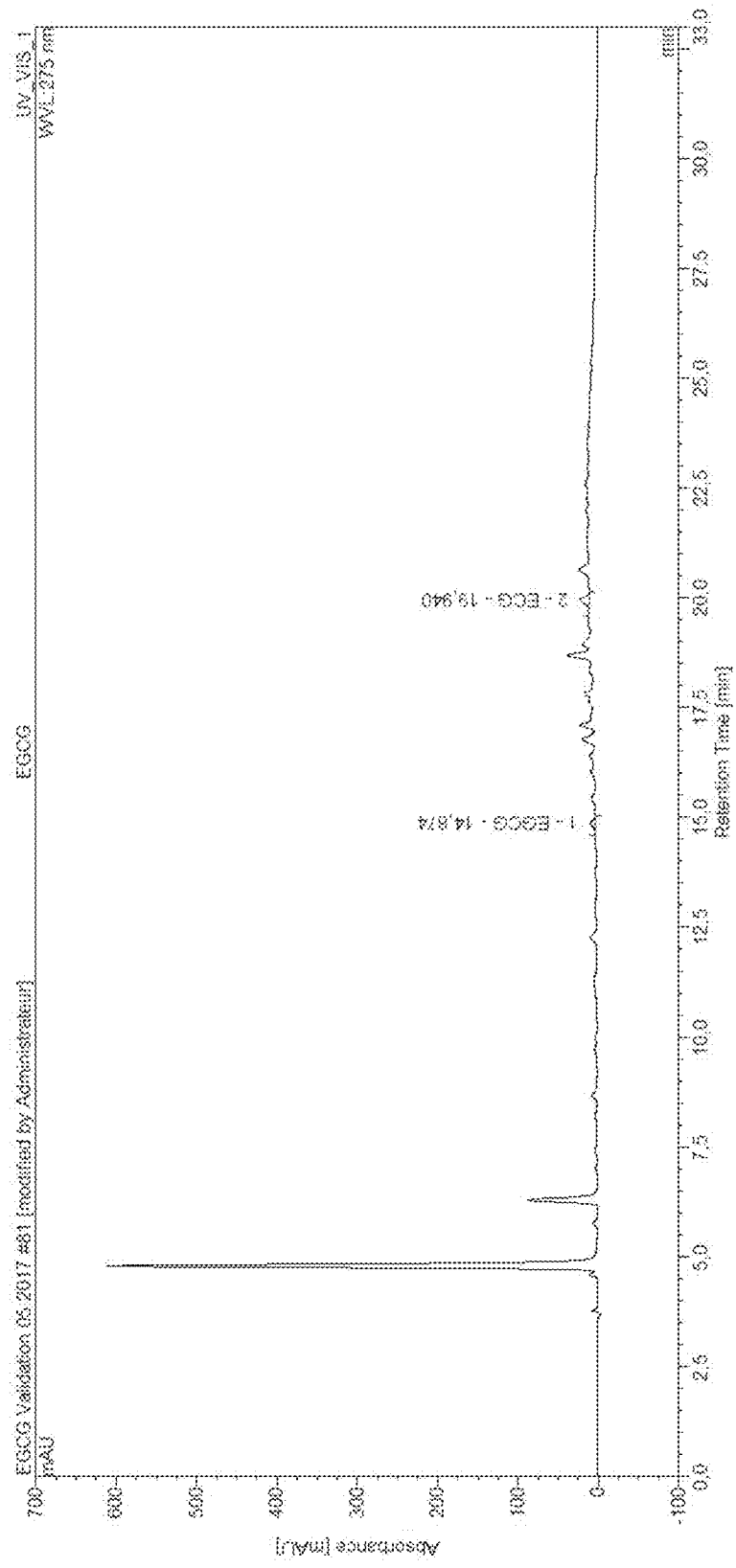

FIGS. 2A, 2B and 2C show stability of a EGCG formulation given in Table 1 below (FIG. 2A) versus that of the EGCG-based solution alone (FIG. 2B). Both solutions were subjected to progressive heating ranging from 25 to 135° C. at a rate of 5° C. per minute. At end of heating, the residues formed from each solution are illustrated in FIG. 2A and are analyzed by high performance liquid chromatography. FIG. 2B is the chromatogram of EGCG formulation given in Table 1. FIG. 2C is the chromatogram of the EGCG-based aqueous suspension free of the other excipients.

Figure 3:
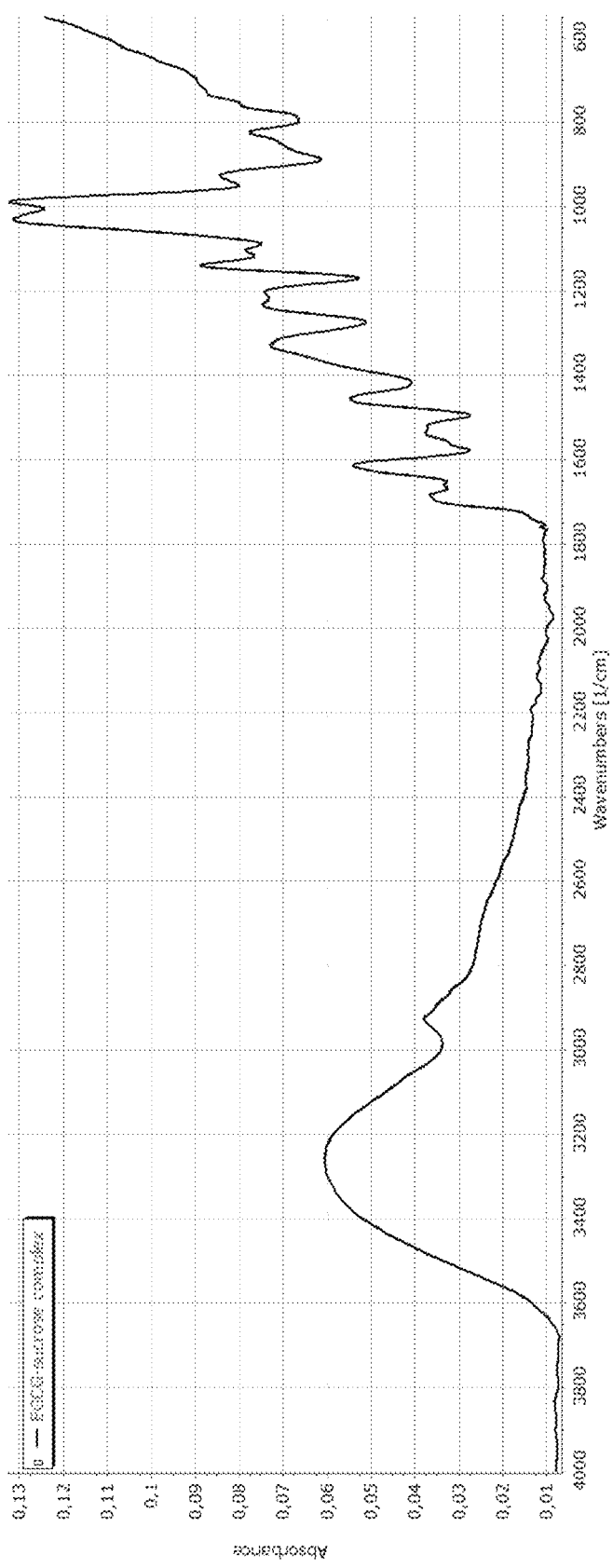

FIG. 3 shows ATR-IR spectra of complex formed by EGCG and sucrose.

Figure 4:
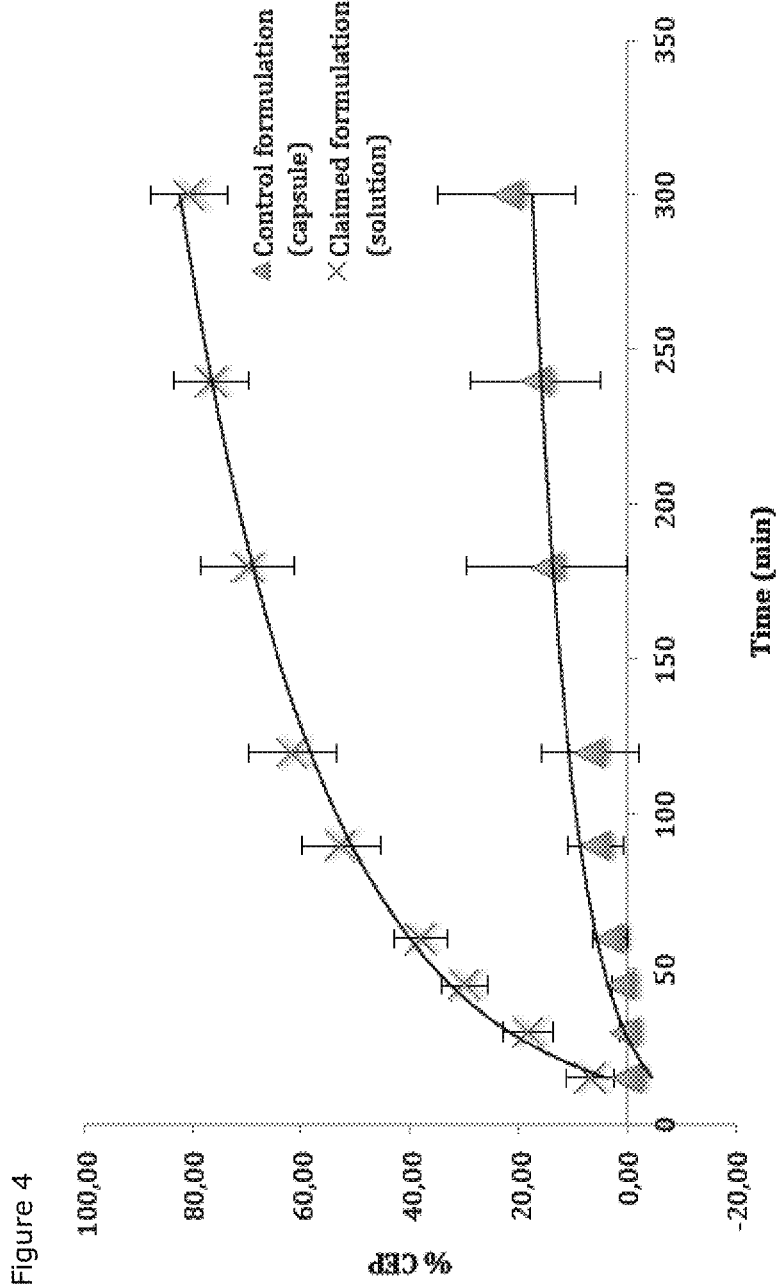

FIG. 4 compares cumulative percentage EGCG permeation (% CEP) over time of the solution of the present invention (claimed formulation) and that of control formulation (capsule) through synthetic dialysis membrane in simulated upper intestinal medium up to 6 h.

Figure 5:
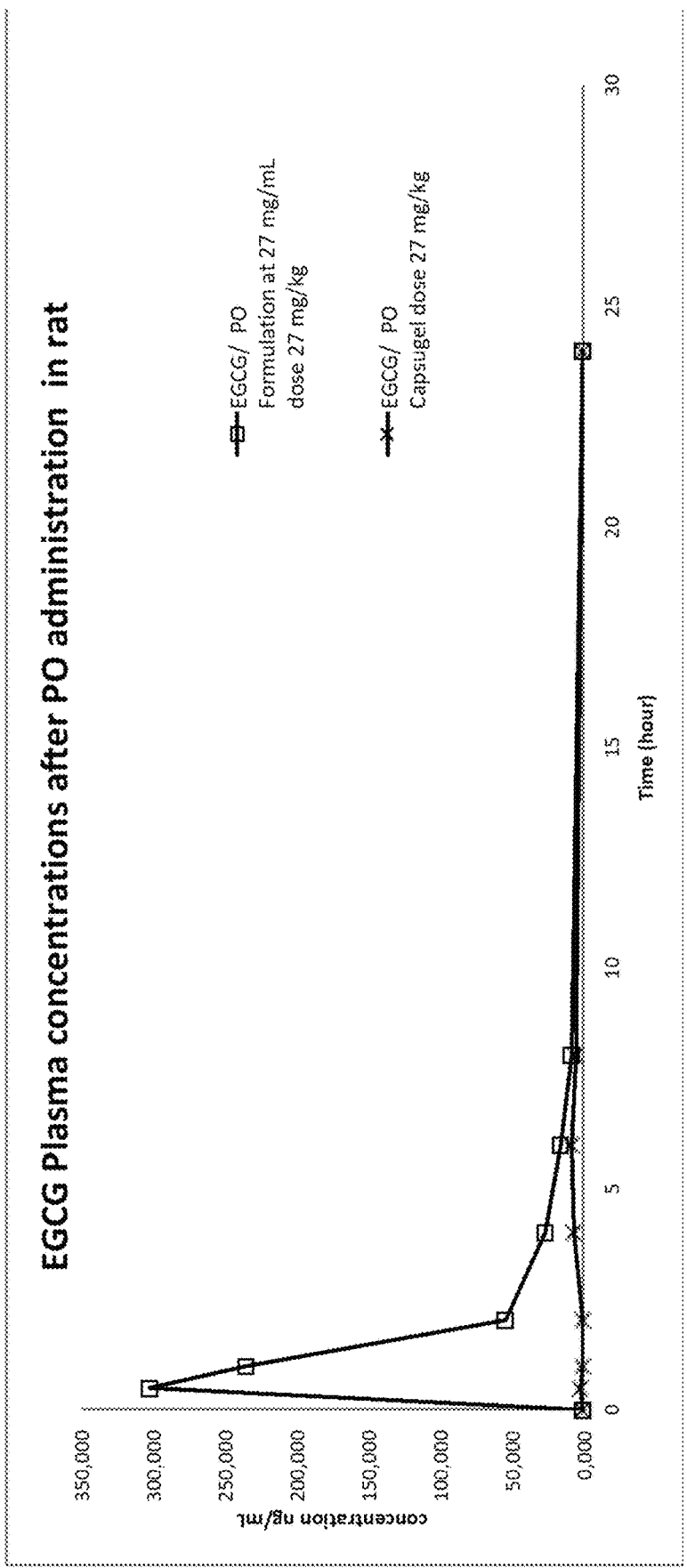

FIG. 5 shows the evolution over time of plasma EGCG concentrations in rat after oral administration of a control formulation (Capsugel dose 27 mg/kg) and a solution of the present invention (Formulation at 27 mg/kg).

EXAMPLES

Example 1

1. Materials and Methods

1.1 Formulation

An EGCG oral solutions is prepared according to the formulation given in table 1 below.

TABLE 1 example EGCG 400 mg/15 mL solution formula

| | Quantities 26.67 mg/mL EGCG oral solution | |
|---|---|---|
| | Unit formula | Formula for 20 L of solution |
| EGCG | 6.7 g | 0.536 kg |
| Citric acid | 0.125 g | 0.010 kg |
| Glucose | 58.5 g | 4.68 kg |
| Sucrose | 25 g | 2 kg |
| Cola flavor | 1.5 g | 0.12 kg |
| Water for injection | Qs 250 mL | Qs 20 L |

EGCG used for preparing said solution is an isolated EGCG extract (>97 w/w of the extract dry). Prior to its use, the active substance was thoroughly controlled to ensure its quality comply with Monograph 2668 (Pharmeuropa June 2017).

Reference standard suspension of EGCG used for the stress stability testing is a water suspension containing uniquely EGCG at a concentration of 26.6 mg/mL. The standard suspension is extemporaneously prepared by dispersing an appropriate amount of an isolated EGCG extract (>97% w/w of the extract dry) in distilled water to afford the said concentration.

Reference standard solution of EGCG used for the long-term and accelerated stability studies is a water solution containing uniquely EGCG at a concentration of 0.26 mg/mL. The standard solution is extemporaneously prepared by dissolving an appropriate amount of an isolated EGCG extract (>97 w/w of the extract dry) in distilled water to afford the said concentration.

1.2 Manufacturing Process

An example of manufacturing process is given below.

Stage 1: Solution Preparation

Step 1: A 20 liter-Pyrex glass vessel is filled to a volume corresponding to ⅓ the final volume of the solution by water for injection.

Step 2: suitable quantities of EGCG, Citric acid, Glucose, Sucrose, Cola flavor according to table 1 are added into water to reach complete dissolution by mixing.

Step 3: water for injection is added to reach final volume.

Stage 2: Filtration

Filtration is carried out by a 1 μ Millipore® filtration cartridge. The filtered solution is stocked in a 20 liter-stainless steel tank with nitrogen inlet for inerting the solution and the headspace of the container.

Stage 3: Filling Into Multiple-Dose Bottle

The solution is filled into 250 mL multiple-dose amber glass bottle. Filled bottle is closed with cap with a polyethylene seal.

1.3 Stress Stability Testing 1 mL of the reference standard suspension and a formulation of the invention disclosed Table 1 before were subjected to a thermal gradient program ranging from 25 to 135° C. at a rate of 5° C. per min. At the end of this exposure, part of each of the residues formed was deposited on a glass slide and the remaining part analyzed by high performance liquid chromatography. The results are displayed in FIG. 2.

1.4 Long-Term and Accelerated Stability Testing

Storage Conditions and Sampling Protocols

The tested batch is prepared according to the formulation of unit dose of 250 ml aforementioned in Table 1.

Reference standard solution of EGCG is a water solution containing uniquely EGCG at a concentration of 0.26 mg/mL.

The tested batch has been stored in accordance with ICH guideline Q1A. Details of the sampling time points for each condition are presented in Table 2. It is diluted ¹⁄₁₀₀ in distilled water prior to HPLC analysis.

TABLE 2

Sampling and storage protocol for primary batch studies

| Time (months) | Storage conditions/container | | |
|---|---|---|---|
| | 2-8° C. Pack | 25° C./60% RH Pack | 40° C./75% RH Pack |
| 1 | + | + | + |
| 2 | + | + | + |
| 3 | + | + | + |
| 4 | + | + | + |
| 5 | + | + | + |
| 6 | + | + | + |
| 9 | + | + | − |
| 12 | + | + | − |
| 18 | + | + | − |

Pack: 250 mL-multiple-dose amber glass bottle (Type III) with a polyethylene cap with polyethylene seal.

Stability Tests and Acceptance Limits

Monitoring appropriate chemical, physical and microbial characteristics during the stability studies and at each time point has allowed assessing the stability of EGCG oral solution.

The chemical stability of EGCG was evaluated by HPLC, validated assay method as a stability indicating method. Said procedure is suitable for the EGCG investigational product assay using an external standard. The assay of EGCG is achieved by comparing the response of a sample solution with the response of EGCG reference standard solution prepared at a similar nominal concentration and analysed in the same way. The sample and reference standard solutions are analysed by gradient reversed phase HPLC and UV detection using a suitable column and chromatography conditions.

HPLC assay uses a liquid chromatograph fitted with a UV detector (variable wavelength or diode array detector) and equipped with column of Interchim® VKR5 C18 (250×4.6.0 mm, 5 μm particle size), or equivalent.

Acetonitrile, acetic acid and pure water are used for prepare mobile phase A (5/95/0.07 v/v/v Acetonitrile/Water/Acetic acid) and mobile phase B (50/50/0.05 v/v/v Acetonitrile/Water/Acetic acid).

Chromatography Procedure

Analyse using suitable chromatographic conditions, for example, those given in Table 3.

TABLE 3

Chromatographic conditions for the assay of EGCG

| Parameter | Setting | | |
|---|---|---|---|
| Mobile phase A | Prepared as described before | | |
| Mobile phase B | Prepared as described before | | |
| Flow rate | 1 mL/min (or as appropriate) | | |
| Oven temperature | 32° C. | | |
| Detection wavelength | 275 nm | | |
| Injection volume | 20 μL | | |
| Gradient programme | The gradient program was set as follows: | | |
| | Temps (min) | A (%) | B (%) |
| | 0 | 90 | 10 |
| | 10 | 80 | 20 |
| | 16 | 60 | 40 |
| | 20 | 50 | 50 |
| | 25 | 50 | 50 |
| | 27 | 60 | 40 |
| | 30 | 90 | 10 |
| | 33 | 90 | 10 |
| Approximate Equilibration time | 45 min | | |
| Approximate retention time of EGCG | ≈14.9 min | | |

System Suitability Criteria

All system suitability criteria are calculated according to the European Pharmacopoeia "Chapter 2.2.46". Specific parameters of the procedure may be modified within pharmacopoeial and validated limits, if necessary, to achieve system suitability.

System suitability criteria should be met are displayed in Table 4.

TABLE 4

System suitability criteria

| System suitability test | Acceptance criteria |
|---|---|
| Tailing factor | Confirm that the tailing factor of the EGCG peak from a reference standard solution injection is not greater than 1.5. |
| System repeatability | Confirm that the relative standard deviation for 3 injections from a reference standard solution is not greater than 2.0% |

Calculation

The percentage of quantity of remained EGCG in diluted sample solution compared to original quantity in that sample is calculated according to following formula $$EGCG\,(\%\ of\ original\ quantity) = \frac{Wstd \times Pstd \times Asam \times D}{Astd \times Vstd \times 26.67} \times 100$$

Wherein:
$A_{std}$=Peak area due to EGCG in reference standard solution
$A_{sam}$=Peak area due to EGCG in diluted sample solution
D=Dilution factor
$W_{std}$=Weight of EGCG taken for the reference standard solution (mg)
$P_{std}$=Purity of reference standard solution (% w/w)
$V_{std}$=Volume of reference standard solution (mL)

1.5. ATR-IR Spectres Image

ATR-IR spectres image of complex sucrose/EGCG is obtained by FTIR-spectroscopy. The experiments were performed on a Perkin-Elmer Spectrum BX FT-IR system based on diffuse reflectance sampling accessories with FT-IR Spectrum v2.00 software. The spectra of the stressed samples were recorded at room temperature in the wavenumber range of 400-4000 cm$^{-1}$ using ATR cell.

2. Results 2.1 Solubility of EGCG Solution According to the Invention

The solubility of EGCG in a solution containing 10% by weight of sucrose is compared to that of EGCG alone in water. The concentration of EGCG in test solution reaches nearly 80 g/L after only 1 hour of dissolution, while the solubility of EGCG in control solution cannot pass 5 g/L after 4 hours of dissolution (FIG. 1).

2.2 Stability of EGCG Solution According to the Invention

Stability test as described in section 1.3 is carried out for a EGCG solution with formulation given in Table 1 and a EGCG-based solution alone. The two solutions were initially clear and transparent. At the end of the applied heating, the residue of the EGCG-based solution alone is black, while a transparent glassy film has been observed in place of the EGCG formulation herein claimed (FIG. 2A). When subjected to analysis by chromatography, the black residue contains practically no more EGCG, whereas the chromatographic profile of the product resulting from the heat treatment of the tested formulation is identical to that of the starting solution, namely that it represents the same as the peak due to EGCG and that of another polyphenol of the green tea initially present (FIGS. 2B and 2C).

The results of long-term stability test are given in table 5 below.

TABLE 5 long-term stability test

| Time (months) | Relative content of EGCG with respect to the initial time (%) for each storage conditions | | |
|---|---|---|---|
| | 2-8° C. | 25° C./60% RH | 40° C./75% RH |
| 0 | 99.8 | 99.8 | 99.8 |
| 1 | 100.0 | 98.4 | 95.8 |
| 2 | 99.4 | 97.7 | 94.2 |
| 3 | 99.7 | 96.6 | 91.7 |
| 4 | 100.0 | 96.4 | 91.5 |
| 5 | 99.8 | 96.3 | 89.1 |
| 6 | 99.6 | 96.8 | 87.6 |
| 9 | 99.6 | 95.2 | 87.5 |
| 12 | 98.4 | 96.1 | NA |
| 18 | 99.2 | 97.7 | NA |

NA: not applicable

The observed storage loss at 25° C./60% RH over 2-8° C. is mainly due to the epimerization of EGCG with the appearance of gallocatechin gallate (GCG), while the difference between 25° C./60% RH and 40° C./75% RH is mainly due to the hydrolysis of the ester function resulting in the appearance of epicatechin and gallic acid.

Long-term stability test shows that the EGCG levels present in the 400 mg/15 mL solution remained unchanged at 2-8° C. and only 5% loss was recorded for the storage at 25° C. By the way, it has been shown that that this loss was largely ascribed to the epimerization of EGCG. Catechin epimerization can be reversible. By the way, catechin transepimers do not have toxic effects but rather similar biological activities to their cis-counterparts.

These results suggest that the formulations developed were able to protect EGCG from auto-oxidation and hydrolysis.

2.3 Structure of Eutectic Complex

ATR-IR spectres image shows the presence of broad absorption in the O—H stretch IR regions and the absence of O—H free stretch peaks (FIG. 3), that suggests that with OH functions of sucrose as acceptors, EGCG would form complexes with sucrose by strong hydrogen bonds OH—O. H-bonding may have caused vibrational modes to vibrated at lower frequencies and/or relative intensities than before, as long as the atoms involved in the vibrational modes are actively participating in H-bonding.

Example 2: In Vitro Permeability Study

In this study, an artificial regenerated cellulose membrane as barrier substitute for Caco-2 cells was used to compare the membrane passage of EGCG from a control formulation and a solution of the present invention. This artificial membrane has the advantage that no cultivation, washing, or pre-incubation steps need to be implemented to carry out the comparison study.

1. Materials and Methods

A EGCG solution with formulation given in Table 1 was used. Control formulation were capsules containing an equivalent amount per unit dose of EGCG Permeability Assessment Using an Artificial Membrane Insert System The permeability study of both EGCG formulations was conducted using a ready-to-use dialysis device Float-A-Lyzer® G2 developed by Spectrum Labs (http://fr.spectrum-labs.com/dialysis/FloatALyzer.html?Lang=English&). The so-called device features a regenerated cellulosic biotechnological ester membrane (molecular weight cutoff, 3.5-5 kDa, membrane diameter, 10 mm and total length, 100 mm). It comprises a donor compartment separated from the receptor (acceptor) one by the cellulosic biotechnological ester membrane. The capacity of the receptor compartment was 600 mL. The area available for diffusion was about 7.85 cm$^2$ (Table 6).

TABLE 6 parameters of the ready-to-use dialysis system used

| Parameters | Values |
|---|---|
| Donor volume (mL) | 5 |
| Acceptor volume (mL) | 600 |
| Hydrodynamics (rpm) | 300 |
| Temperature (° C.) | 37 |
| Surface Area (cm$^2$) | 7.85 |

Filling Solutions of the Donor and Acceptor Compartments

The composition of the solution used to fill the donor compartment mimics that composing the duodenal medium, while the diffusion fluid is a $10^{-4}$ mol L$^{-1}$ phosphate buffer solution adjusted to pH 5.5.

The simulated duodenum medium, as proposed by Tenore et al (*Food Chemistry* 169 (2015) 320-326), is made up with a $10^{-3}$ mol L$^{-1}$ phosphate buffer solution, pancreatin (0.4 mg mL$^{-1}$) and bile salts (2.5 mg mL$^{-1}$). The final mixture is adjusted to pH 6.8 using hydrochloric acid.

In Vitro Comparative Permeation Studies

The donor compartment was filled separately with each formulation, either 750 µL of the claimed formulation or one capsule containing 20 mg EGCG and lactose. The donor cell was covered with an aluminium foil to prevent evaporation of vehicle. The fluid, in the receptor chamber, was maintained at 37±0.5° C. and stirred continuously at a very low speed (30 rpm), using thermostatically controlled magnetic stirrer with Teflon coated bead. Care was taken to make sure that no air bubbles were present inside the receptor compartment.

Aliquot (1 mL each time) was withdrawn periodically at pre-set time from the abovementioned receiver cell, which was 10 times diluted with $10^{-4}$ mol $L^{-1}$ phosphate buffer solution (pH 5.5) and filtered through 0.45 µm filter. EGCG content was determined by HPLC. The diffusion fluid of the same volume was pre-warmed at 37° C. The volume of withdrawn samples was replaced by pre-warmed diffusion fluid into the diffusion cell to keep the volume constant so that sink condition could be maintained. Experiment was carried out up to 6 h. The rates of drug permeation at different time points were calculated in each case.

Data Analysis

Data obtained from the permeability study for each formulation, were used to calculate % CEP, $P_{app}$ (apparent permeability coefficient) and ER.

$P_{app}$ and ER were calculated by following the standard formulae (*Arch Appl Sci Res* 2010; 2:31-42; *Eur J Pharm Sci* 1994; 2:311-30; *Asian J Pharm Clin Res* 2010; 3:31-4):

Permeability coefficient ($P_{app}$):

$$P_{app}=(VA/\text{area}\times\text{time})\times([EGCG]\text{acceptor}/[EGCG]\text{donor})$$

where, VA=Volume in acceptor compartment, Area=Surface area of the membrane, Time=Total transport time

ER:

$$ER=P_{app} \text{ of the formulation of the present application}/P_{app} \text{ of control (capsule)}.$$

HPLC Analysis

The diluted samples were analysed by HPLC, validated assay method as a stability indicating method described above in Example 1. Said procedure is suitable for EGCG assay using an external standard. The assay of EGCG is achieved by comparing the response of a sample solution with the response of EGCG reference standard solution prepared at a similar nominal concentration and analysed in the same way. The sample and reference standard solutions are analysed by gradient reversed phase HPLC and UV detection using a suitable column and chromatography conditions.

2. Results

Permeability study of the two formulations of EGCG (the solution of the present invention versus control, i.e. EGCG in capsule) was carried out using cellulosic biotechnological ester membrane as diffusional membrane and simulated intestinal medium as diffusional fluid at different time points up to 6 h.

The results of this investigation have been mentioned in Tables 7 and 8. The values of % CEP and $P_{app}$ were determined after 6 h in cases of all samples. These values were least/minimum in case of control formulation (capsule), while the solution of the present invention showed maximum values. Interestingly, the $P_{app}$ value found in this study for the control formulation turns out to be equivalent to that found by Zhang et al (*International Journal of Pharmaceutics* 287 (2004) 1-12) investigating GTC intestinal absorption and disposition by Caco-2 monolayer model, so that which demonstrates transposability between our artificial membrane model and the caco-2 cell model.

Above-mentioned results have also been depicted in different graphs by taking % CEP at different time points versus time (FIG. 4).

TABLE 7

% CEP of EGCG from control (capsule) and the solution of the present invention using synthetic dialysis membrane

| | Control formulation (capsule) n = 3 | | Solution of the present invention n = 7 | |
|---|---|---|---|---|
| Times(h) | Mean (%) | SD | Mean (%) | SD |
| 15 | 0.00 | 0.00 | 6.87 | 4.31 |
| 30 | 0.54 | 0.71 | 18.38 | 4.57 |
| 45 | 1.21 | 1.55 | 29.96 | 4.21 |
| 60 | 3.16 | 3.25 | 38.03 | 5.00 |
| 90 | 5.86 | 5.09 | 52.67 | 7.31 |
| 120 | 6.78 | 9.09 | 61.65 | 8.12 |
| 180 | 14.86 | 14.83 | 69.86 | 8.66 |
| 240 | 16.83 | 11.99 | 76.61 | 6.87 |
| 300 | 21.99 | 12.76 | 80.54 | 7.03 |

TABLE 8 in vitro permeability profiles of the samples of EGCG through synthetic dialysis membrane up to 6 h

| Samples | % CEP | Papp (cm/s) × $10^{-7}$ | ER |
|---|---|---|---|
| Control formulation (capsule) | 21.99 | 1.29 | — |
| Solution of the invention | 80.54 | 4.74 | 3.67 |

The overall results of this study show that the solution of the present invention gave the best permeation result to control with an ER of ≈4.

These results clearly contribute to providing proof of concept that the solution of the present invention can improve the bioavailability of EGCG, paving the way for improved clinical efficacy.

Example 3: Stability of the Aqueous Solutions With Respect to Light Irradiation

A EGCG solution with formulation given in Table 1 was allocated in in 15 mL Pyrex glass vials, hermetically sealed and exposed to light using a xenon test chamber Q-SUN Xe-1 operating in window mode. The light beam, presenting a characteristic spectrum ranging from 300 to 800 nm, was delivered at an intensity of 1.50 W $m^{-2}$. Aliquots of samples were withdrawn after 1-h exposure. No change in coloration was noted on the solution. Moreover, the chromatographic profile of the tested solution was identical to that of the starting solution, namely that it represents the same as the peak due to EGCG and that of another polyphenol of the green tea initially present (ECG).

Example 4: Plasma Concentrations of EGCG in Rat

This test was performed to compare plasma concentrations and total area under the curver ($AUC_{total}$) obtained after oral administration in rats of the formulation of EGCG of the present invention with capsules containing EGCG.

1. Materials and Methods

Animals 9 male Sprague-Dawley rats with weight at least of 300 g were used. Janvier Labs supplied them.

The in vivo test was located in the rodent area of Eurofins ADME BIOANALYSES. There is entirely artificial lighting in the room with a controlled cycle of 12 hours light, 12 hours dark. It is air conditioned by a system designed to maintain normal conditions. An ear tag identified each animal. The animals were examined for general health and welfare. The animals had free access to food and water during the experiment.

Process, treatment and euthanasia were conducted according to the current procedures in use at Eurofins ADME BIOANALYSES.

Analytical Test

The analytical test was based on the method described by de Lourdes et al (*J. Agric. Food Chem.* 2007, 55, 8857-8863).

The molecular and daughter ions were selected for each molecule after direct infusion into the MS-MS system. The analytical method consisted of a precipitation of the proteins by addition of appropriate solvent followed by a LC-MS/MS analysis. According to the expected sensitivity, at least 8 calibration standards were used for the preparation of the calibration curve in plasma. The corresponding correlation coefficient were calculated and had to be higher than 0.75 to continue with the in vivo test.

The calibration range tested will be 4 to 5000 ng/mL of EGCG in plasma. The difference between the mean concentration observed and the nominal concentration was used to estimate the deviation of the method.

Formulation Administered for the In Vivo Test

The two EGCG formulations administered in the experience (a control formulation and a solution of the present invention prepared by the Pharmacy of Henri Mondor Hospital) are listed in table 9 below.

TABLE 9

EGCG formulation for in vivo test

| Reference compounds | Route of administration | Vehicle | Concentration (mg/mL) | Volume of administration (mL/kg) | Selected dose (mg/kg) |
|---|---|---|---|---|---|
| EGCG | PO | No vehicle Administration via at least 1 Capsugel ® | — | — | 27 |
| EGCG | PO | Prepared by the Pharmacy of the Henri Mondor Hospital | 27 | 1* | 27 |
| — | No administration | — | — | — | 0 |

*In order to increase the volume administered and optimize precision, the rats used had a minimum weight of 300 g.

The formulations were stored at room temperature. The formulations were kept under magnetic stirrer during administration.

Blood Sampling and Sampling Times

At prescribed times, blood were collected and treated as indicated below:
 Site of collection: sinus retro-orbital using a capillary tube
 Volume of blood collected: 0.300 mL minimum per time-point
 Anticoagulant: lithium heparin The exact sampling times were recorded at each blood sample.

The blood samples were centrifuged at 2500 rpm at 10° C. and the plasma removed and placed into labelled polypropylene tubes.

These individual plasma samples were stored frozen (−20° C.±5° C.) until analysis.

Sampling times for two above-mentioned formulations are listed in the table 10.

TABLE 10 sampling times

| Reference compound | Route of administration | Selected dose (mg/kg) | Animals: rat SD | Plasma sampling time |
|---|---|---|---|---|
| EGCG | PO via Capsugel ® | 27 | 3 | 30 min, 1 h, 2 h, 4 h, 6 h, 8 h, 24 h |
| EGCG | PO via liquid formulation | 27 | 3 | 30 min, 1 h, 2 h, 4 h, 6 h, 8 h, 24 h |
| — | no administration | 0 | 3 | 30 min, 1 h, 2 h, 4 h, 6 h, 8 h, 24 h |

2. Results

Concentration and $AUC_{total}$ results are summarized in the table 11 below.

The FIG. 5 illustrates the evolution of plasma EGCG concentrations over time.

As these results show, the systemic exposure resulting from the formulation resulting from the invention is, at equal doses administered, much higher than that of the traditional capsule form containing 100% of the EGCG powder. Indeed, the total AUC ratio per dose is 18 in favour of the formulation resulting from the invention.

| | Sampling time (h) | Mean | AUCt partial (ng/mL*h) | $AUC_{total}$ (ng/mL*h) | $AUC_{total}$ per Dose |
|---|---|---|---|---|---|
| No administration | | | | | |
| Plasma (ng/mL) | 0 | <LOQ | | | |
| | 0.5 | <LOQ | 0.000 | 21.166 | — |
| | 1 | 28.221 | 7.055 | | |
| | 2 | <LOQ | 14.110 | | |
| | 4 | <LOQ | 0.000 | | |
| | 6 | <LOQ | 0.000 | | |
| | 8 | <LOQ | 0.000 | | |
| | 24 | <LOQ | 0.000 | | |
| EGCG/PO Capsugel dose 27 mg/kg | | | | | |
| Plasma (ng/mL) | 0 | <LOQ | | | |
| | 0.5 | 1.959 | 0.490 | 33.769 | 1.053 |
| | 1 | <LOQ | 0.490 | | |
| | 2 | <LOQ | 0.000 | | |
| | 4 | 6.080 | 6.080 | | |
| | 6 | 7.910 | 13.989 | | |

-continued

| | Sampling time (h) | Mean | AUCt partial (ng/mL*h) | AUC$_{total}$ (ng/mL*h) | AUC$_{total}$ per Dose |
|---|---|---|---|---|---|
| EGCG/PO Formulation at 27 mg/mL dose 27 mg/kg | 8 | 4.812 | 12.721 | | |
| | 24 | <LOQ | 38.495 | | |
| Plasma (ng/mL) | 0 | <LOQ | | | |
| | 0.5 | 302.405 | 75.601 | 497.401 | 18.422 |
| | 1 | 234.270 | 134.169 | | |
| | 2 | 53.267 | 143.769 | | |
| | 4 | 26.416 | 79.683 | | |
| | 6 | 15.119 | 41.536 | | |
| | 8 | 7.524 | 22.643 | | |
| | 24 | <LOQ | 60.193 | | |

The invention claimed is:

1. A stable pharmaceutical or dermo-cosmetic aqueous solution comprising:
   13-107 mg/ml of epigallocatechin gallate,
   at least one disaccharide,
   0.1-1.0 mmol/l of at least one chelating agent,
   a pharmaceutically acceptable or dermo-cosmetically acceptable pH-modifying agent, and
   wherein said solution is at a pH in a range of 3.0 to 4.0 and the molar ratio of epigallocatechin gallate/disaccharide is from 0.1 to 0.8.

2. The pharmaceutical or dermo-cosmetic aqueous solution according to claim 1, wherein the disaccharide is chosen from sucrose and trehalose.

3. The pharmaceutical or dermo-cosmetic aqueous solution according to claim 1, further comprising at least one antioxidant agent suitable for the aqueous systems and compatible with acidic pH, chosen from ascorbic acid, erythorbic acid, monothioglycerol, sodium metabisulfite and sodium bisulfate, and reducing sugar.

4. The pharmaceutical or dermo-cosmetic aqueous solution according to claim 1, wherein said solution is exempt of organic solvent.

5. The pharmaceutical or dermo-cosmetic aqueous solution according to claim 1, wherein said solution further comprises an organic solvent chosen from ethanol, propylene glycol, glycerol, and PEG 400.

6. The pharmaceutical or dermo-cosmetic aqueous solution according to claim 1, wherein the chelating agent is chosen from citric acid, calcium disodium edetate, disodium edetate, fumaric acid, malic acid, maltol and pentetic acid.

7. The pharmaceutical or dermo-cosmetic aqueous solution according to claim 1, wherein the pharmaceutically acceptable pH-modifying agent is chosen from acetic acid, adipic acid, ammonium carbonate, ammonium hydroxide, ammonium phosphate, citric acid, diethanolamine, fumaric acid, hydrochloric acid, malic acid, nitric acid, proprionic acid, potassium acetate, potassium bicarbonate, potassium chloride, potassium citrate, potassium metaphosphate, potassium phosphate, sodium acetate, sodium bicarbonate, sodium carbonate, sodium citrate, sodium glycolate, sodium hydroxide, sodium lactate, sodium phosphate, sodium proprionate, succinic acid, sulfuric acid, tartaric acid, and triethanolamine.

8. The pharmaceutical or dermo-cosmetic aqueous solution according to claim 1, comprising:
   13-107 mg/ml, of epigallocatechin gallate
   0.05-3.0 mg/ml, of citric acid,
   25-140 mg/ml, of sucrose, and
   optionally, 25-250 mg/ml, of glucose and/or fructose.

9. The pharmaceutical or dermo-cosmetic aqueous solution according to claim 8, comprising:
   27 mg/ml of epigallocatechin gallate
   0.1 mg/ml of citric acid
   100 mg/ml of sucrose, and
   100 mg/ml of glucose.

10. The pharmaceutical aqueous solution of claim 1, a unit dose of epigallocatechin gallate comprising said pharmaceutical aqueous solution or a solid composition of said pharmaceutical aqueous solution or a solid composition of said unit dose for its use as a medicament in the treatment of cancers, cardiovascular disorder, diabetes, neurodegenerative diseases, or dermatological diseases.

11. A unit dose of epigallocatechin gallate comprising the pharmaceutical or dermo-cosmetic aqueous solution according to claim 1.

12. The unit dose according to claim 11, wherein said unit dose has a volume in the range of 5-30 ml.

13. The unit dose according to claim 11, wherein epigallocatechin gallate has a weight in the range of 200-1600 mg.

14. A solid composition resulting from any water removal process of the pharmaceutical or dermo-cosmetic aqueous solution of claim 1 or of a unit dose of epigallocatechin gallate comprising said pharmaceutical or dermo-cosmetic aqueous solution.

15. A dermo-pharmaceutical product comprising the pharmaceutical aqueous solution of claim 1, a unit dose of epigallocatechin gallate comprising said pharmaceutical aqueous solution or a solid composition of said pharmaceutical aqueous solution or a solid composition of said unit dose.

16. A dermo-cosmetic product comprising the dermo-cosmetic aqueous solution of claim 1 or a solid composition of said dermo-cosmetic aqueous solution.

* * * * *